United States Patent [19]

Wells

[11] Patent Number: 4,670,220

[45] Date of Patent: Jun. 2, 1987

[54] SAMPLE VALVE FOR SOLUTE MODULATED SYNCHRONOUS DETECTION

[75] Inventor: Gregory J. Wells, Suisun, Calif.

[73] Assignee: Varian Associates, Inc., Palo Alto, Calif.

[21] Appl. No.: 871,158

[22] Filed: Jun. 2, 1986

Related U.S. Application Data

[63] Continuation of Ser. No. 585,624, Mar. 7, 1984, abandoned.

[51] Int. Cl.$^4$ ............................................. B01L 11/00
[52] U.S. Cl. ........................................ 422/103; 73/23; 73/27 R; 73/864.81; 422/89; 436/161
[58] Field of Search ................... 422/89, 103; 436/161; 73/23.1, 27 R, 864.81

[56] References Cited

U.S. PATENT DOCUMENTS

| | | | |
|---|---|---|---|
| 3,357,233 | 12/1967 | Roof | 73/23.1 |
| 3,362,228 | 1/1968 | Stuben | 422/103 |
| 4,231,990 | 11/1980 | Jottier | 422/103 |
| 4,254,654 | 3/1981 | Clouser et al. | 73/27 R |
| 4,388,411 | 6/1983 | Lovelock | 436/149 |

OTHER PUBLICATIONS

Wade et al, "Fluidic Logic Sampling and Injection System for Gas Chromatography", *Analytical Chem.*, vol. 44, No. 1, (1/72), pp. 131-139.

*Primary Examiner*—Peter Chin
*Attorney, Agent, or Firm*—Stanley Z. Cole; Gerald M. Fisher; David Schnapf

[57] ABSTRACT

A sample valve for solute modulated synchronous detection alternately directs into a detector a sample gas stream $F_1$ which passes through a modulator cell and a reference gas stream $F_2$ which passes through a balance cell. The sample valve is made of a symmetrically structured chamber with inlets and outlets. An ordinary valve causes a control gas to stream into the chamber alternately though one of two openings to exit openings of the chamber are synchronously opened and closed so that gas streams $F_1$ and $F_2$ are alternately led into the detector and out of the system.

10 Claims, 3 Drawing Figures

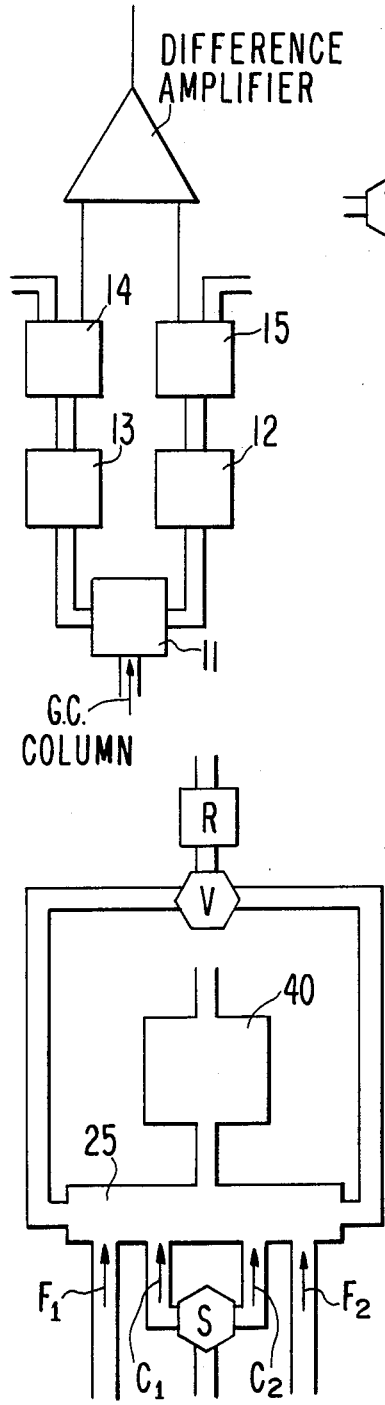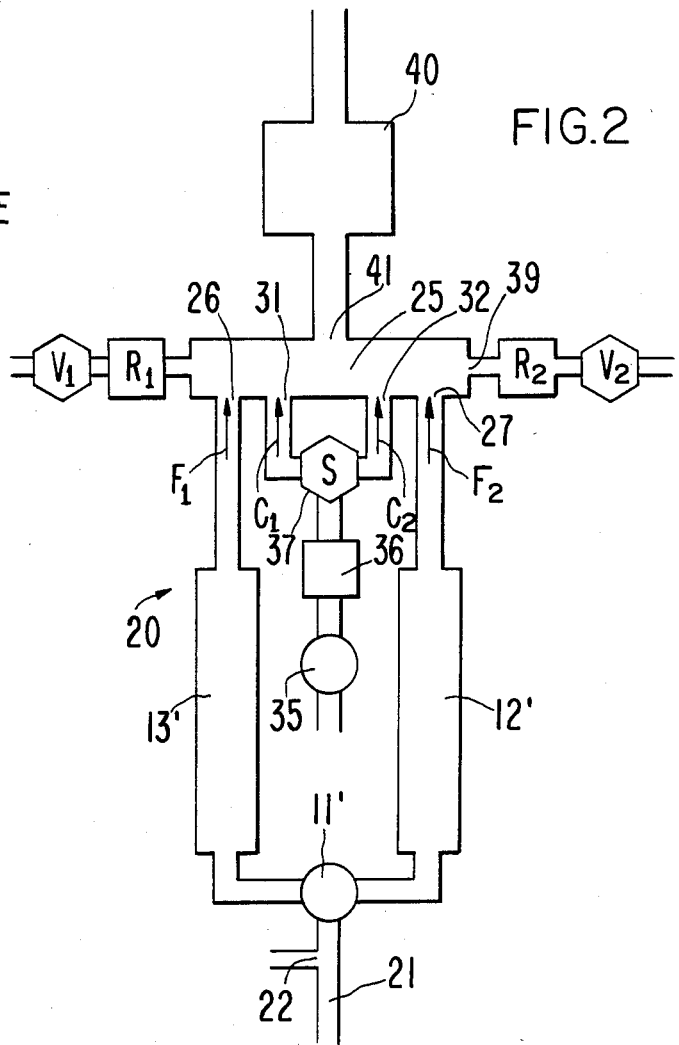

SAMPLE VALVE FOR SOLUTE MODULATED SYNCHRONOUS DETECTION

This application is a continuation of application Ser. No. 585,624, filed 03/07/84, now abandoned.

BACKGROUND OF THE INVENTION

This invention relates to a sample valve for solute modulated synchronous detection and more particularly to a means for alternately sampling two gas streams and causing the resultant segments of gas to enter a gas chromatographic detector.

It has been known in physical measurements to recover weak signals from overwhelming noise, or to improve the signal-to-noise ratio by modulating the signal. Subsequent narrow band amplification followed by synchronous demodulation can result in a reduction in noise often by several orders of magnitude. It has also been known that the noise reduction is best obtained if only the signal of interest is modulated and not the noise.

This principle of modulation has also been applied to chromatography. According to the so-called in-line solute modulation scheme described, for example, in U.S. Pat. No. 4,019,863 issued Apr. 26, 1977 to A. Jenkins, et al., and U.S. Pat. No. 4,260,884 issued Apr. 7, 1981 to J. E. Lovelock, the sample modulation is accomplished by periodically modifying, or destroying by electron attachment, the component of interest inside a modulator cell (or solute switch) which is similar to an electron capture detector (ECD), but has a much higher density of electrons available to attach to compounds. The modulator cell functions by periodically destroying compounds that respond strongly (the signal), but not destroying weakly responding compounds (the noise). The compounds that attach electrons are subsequently destroyed by the combination with the positive ions in the cell and thus cannot be detected in the detector such as an ECD placed immediately downstream. The scheme, however, is not satisfactory in that the degree and maximum frequency of modulation are limited by the volume of the modulator cell and the flow rate of gas therethrough. In one aspect of the recent studies, it has been shown that the constraints of improved signal-to-noise ratio and response time require that high modulation frequencies be used. Such high frequencies can be obtained only by utilizing small cell volumes and high gas flow rates. In another aspect, however, it is known that the sample must remain inside the cell as long as possible in the solute destruction portion of the modulation cycle. This naturally requires large volumes and/or slow flow rates.

In FIG. 1, there is shown schematically a detector system developed as a result of an attempt to solve the aforementioned problem of the in-line solute modulation scheme. The sample eluting from a gas chromatographic column (not shown) is split in half by a linear effluent splitter 11 into two cells 12 and 13. One cell (balance cell) 12 is passive in that no change occurs to the sample. In the other cell (modulator cell) 13, however, the component of interest in the sample is selectively destroyed, for example, by electron attachment as explained above. The sample is thereby prevented from responding in the ECD 14 which follows the modulator cell 13. Another detector 15 follows the balance cell 12 and the difference between the output of the two identical detectors 14 and 15 is shown as the final signal. Since the compositions of the gas streams leaving the modulator cell 13 and the balance cell 12 are the same except that the component of interest has been inhibited from responding or removed from the stream leaving the modulator cell 13, only this component produces a difference signal. This method based on measurements of difference in the DC mode involves a problem that precise matching of the detector characteristics is indispensible.

The aforementioned required of precise detector balancing can be obviated if only one detector is used, the gas streams from the two cells 12 and 13 of FIG. 1 being alternately directed into one detector. This method is described in U.S. Pat. No. 4,388,411 issued June 14, 1983 to J. E. Lovelock who had already published its basic concept in J. Chromatogr., 112, 29 (1975), stating therein that the full possibilities of the method would probably await the development of a reliable means of switching carrier-gas flow between two or more paths.

SUMMARY OF THE INVENTION

It is therefore an object of the present invention to provide a reliable means of switching a gas flow between two or more paths.

It is another object of the present invention to provide a sample valve for solute modulated synchronous detection in which the gas flow is unidirectional.

It is still another object of the present invention to provide a sample valve for solute modulated synchronous detection through which the sample does not flow directly.

BRIEF DESCRIPTION OF THE DRAWINGS

FIG. 1 illustrates schematically a gas chromatographic detector system according to a conventional in-line solute modulation scheme.

FIG. 2 illustrates a solute modulated synchronous detection system using a sample valve of the present invention.

FIG. 3 illustrates another solute modulated synchronous detection system using a sample valve of the present invention.

DETAILED DESCRIPTION OF THE INVENTION

In FIG. 2, there is shown schematically a solute modulated synchronous detection system 20 using a sample valve means of the present invention. The parts which are structurally no different from those shown in FIG. 1 are assigned like numerals. Thus, the sample eluting from a gas chromatographic column (not shown) is led into the system 20 through an inlet port 21 which may be provided with a side port 22 for introducing a make-up gas into the system 20 and the flow is evenly divided into two streams designated $F_1$ and $F_2$ by a linear effluent splitter 11', stream $F_1$ flowing through a modulator cell 13' and stream $F_2$ flowing through a balance cell 12'. As explained in connection with FIG. 1, the two streams $F_1$ and $F_2$ are matched and the same except that component of interest is inhibited from responding or removed from the stream $F_1$ (totally or only partially) leaving the modulator cell 13' while the component of interest flowing through the balance cell 12' is thereby totally unaffected. Streams $F_1$ and $F_2$, respectively from the modulator and balance cells 13' and 12', are lead into a control chamber 25 respectively through openings 26 and 27. The control chamber 25 is preferably symmetrical in structure with respect to a central plane of symmetry. The openings 26 and 27 are provided symmetrically with respect to this plane of symmetry and the control chamber 25 is further provided with two more symmetrically located openings 31 and 32 between the openings 26 and 27. A control gas is introduced into the control chamber 25 by passing through a pressure regulator 35, a restrictor 36, and a switch valve 37 (S). The switch valve 37 may be of a usual mechanical type and determines whether the control gas should enter the control chamber 25 through the opening 26 or through the opening 27. The control gas flows from the switch valve 37 into the control chamber 25 through the openings 31 and 32 will be denoted $C_1$ and $C_2$, respectively, for convenience.

Two symmetrically located outlets 38 and 39 are provided to the control chamber 25 on opposite sides of the group of openinge 26, 27, 31 and 32. The flows of gas out of the control chamber 25 through outlets 38 and 39, respectively, pass through restrictors $R_1$ and $R_2$ and reach valves $V_1$ and $V_2$. A detector 40 is connected to the control chamber 25 through a central exit opening 41. The valves S, $V_1$ and $V_2$ are adapted to be operable in a mutually synchronized relationship as described below.

For explanation of the operation, let us assume first that the flow impedance of the restrictors $R_1$ and $R_2$ is the same as that due to the detector 40. Stream $F_1$ can then be directed into the detector 40 by closing the valve $V_1$, opening the valve $V_2$ and setting the valve S so that the control flow $C_2$ will separate the streams $F_1$ and $F_2$ because this control flow will force $F_1$ into the detector 40 and $F_2$ out through the valve $V_2$. During the next stage in the operation cycle, the mechanical switch valve 37 changes its setting so as to stop $C_2$ and allow $C_1$ to flow. Simultaneously, the valve $V_1$ opens and the valve $V_2$ closes so that the stream $F_1$ will be forced out through the valve $V_1$ and the stream $F_2$ will be forced into the detector 40.

One of the advantages of this means of switching is that the sample does not flow directly through a mechanical valve prior to entering the detector. Mechanical valves generally cannot operate at high temperatures and the valve seats are sources of contamination. Another advantage is that the flow through the detector is always unidirectional. If the gas flow must stop and reverse directions during each cycle, there results turbulence within the cell and this limits the maximum modulation frequency and hence the response time and the improvement in signal-to-noise ratio.

The disclosure given above, however, must be regarded as illustrative rather than as limiting. It is to be understood that many changes can be made thereon without departing from the scope of this invention. For example, the valves $V_1$ and $V_2$ may be united into a single valve V with two inputs and one output so that the system may look as shown schematically in FIG. 3. It is not necessary that the restrictors $R_1$ and $R_2$ have the same flow impedance as the detector 40. The restriction may be less than that of the detector 40. In such a case, it can be made sure that the flow will go into the detector 40 by increasing the control flow $C_1$ and $C_2$ with respect to $F_1$ and $F_2$. The relative positions of the openings 26, 27, 31, 32, 38 and 39 need not be exactly as shown in FIG. 2 as long as the desired flow patterns as described above can be established by the operation of the valves S, $V_1$ and $V_2$ or V. The scope of the invention is defined only by the following claims.

What is claimed is:

1. A sample valve for use with a pressurized source of control gas for alternately directing two substantially equal, constantly flowing, laminar gas streams to a detector, comprising;

a valve body comprising an enclosed chamber having no moving parts, first and second sample inlets having equal flow impedance through which said tube gas streams enter the chamber, first and second control gas inlets having equal flow impedance through which said control gas enters said chamber, a first switching means for directing the control gas into said chamber alternately through the first and second control gas inlets, a detector outlet, for channeling a portion of the gas within the chamber to said detector, first and second nondetector outlets having equal flow impedance for channeling a portion of the gas from the chamber, a second switching means for alternately opening and closing the first and second nondetector outlets, so that the first nondetector outlet is open when the second nondetector outlet is closed and the first nondetector outlet is closed when the second nondetector outlet is open, means for synchronizing said first and second switching means to cycle at the same frequency, and means to direct the gas from the first sample inlet to the detector outlet and the gas from the second sample inlet to the first nondetector outlet when the first control gas inlet is open, and to direct the gas from the second sample inlet to the detector outlet and the gas from the first sample inlet to the second nondetector outlet when the second control gas inlet is open, whereby both of the sample gas streams move smoothly and with a minimum of turbulence when within the chamber and when within the detector outlet.

2. The sample valve of claim 1, wherein the chamber is symmetrical, the detector outlet is positioned on an axis of symmetry of the chamber, and the control gas inlets, the sample inlets and the non-detector outlets are symmetrically positioned about said axis of symmetry.

3. The sample valve of claim 2 wherein all of said outlets and inlets lie in a single plane.

4. The sample valve of claim 2 wherein the distance between the non-detector outlets is greater than the distance between said sample inlets, and the distance between the sample inlets is greater than the distance between the control gas inlets.

5. The sample valve of claim 4, wherein said first switching means comprises a mechanical valve having one inlet connected to said control gas source and two outlets connected to said first and second control gas inlets.

6. The sample valve of claim 4, wherein said second switching means comprises at least one mechanical valve.

7. The sample valve of claim 6 wherein said second switching means comprises one mechanical valve having two inlets and one outlet.

8. The sample valve of claim 6 wherein said second switching means comprises two mechanical valves each having one inlet and one outlet.

9. The sample valve of claim 4 wherein the flow impedance of the detector outlet is equal to the flow impedance of each non-detector outlet.

10. The sample valve of claim 4 wherein the flow impedance of the detector outlet is greater than the flow impedance of each non-detector outlet.

* * * * *